United States Patent [19]
Passi

[11] Patent Number: 5,952,577
[45] Date of Patent: Sep. 14, 1999

[54] ULTRASONIC IMAGING SYSTEM

[75] Inventor: Garri S. Passi, Ashdod, Israel

[73] Assignee: Sonotron Ltd., Yavne, Israel

[21] Appl. No.: 08/897,609

[22] Filed: Jul. 21, 1997

[51] Int. Cl.[6] .................................................. A61B 8/00
[52] U.S. Cl. ........................................... 73/618; 600/445
[58] Field of Search ............................. 73/599, 600, 602,
    73/624, 625, 626, 632, 633, 634, 618, 621;
    600/444, 445, 463

[56] References Cited

U.S. PATENT DOCUMENTS

| 4,160,386 | 7/1979 | Jackson et al. | 73/625 |
| 4,821,575 | 4/1989 | Fujikake et al. | 73/626 |
| 5,203,337 | 4/1993 | Feldman | 128/662.06 |
| 5,337,611 | 8/1994 | Fleming et al. | 73/622 |
| 5,398,690 | 3/1995 | Batten et al. | 128/660.03 |
| 5,425,370 | 6/1995 | Vilkomerson | 128/662.06 |
| 5,524,627 | 6/1996 | Passi | 128/660.09 |

Primary Examiner—Hezron Williams
Assistant Examiner—Helen C. Kwok
Attorney, Agent, or Firm—Mark M. Friedman

[57] ABSTRACT

An ultrasonic imaging system for imaging an object. The system includes a mechanism for designating an ultrasonic probe swiveling angle threshold beyond which the ultrasonic probe does not adequately image the scanned object, and an echo amplitude correction apparatus for correcting the amplitude of a received echo by normalizing such amplitude to the value of a previously recorded echo of higher amplitude. Furthermore, the system includes a mechanism for monitoring acoustic coupling, which includes a low frequency noise level selection apparatus for manually selecting the power at which a low frequency reference noise is generated by a vibrator, and a low frequency noise receiving crystal located in the probe holder of the ultrasonic probe, for receiving the low frequency reference noise signal. In addition, the system includes a probe location monitoring apparatus, including two mobile non-directional transceivers in the form of an air acoustic dipole, for determining ultrasonic probe location by triangulation; a mechanism for designating the displacement between the transceivers; and a mechanism for designating the radius of curvature of the object being scanned.

13 Claims, 7 Drawing Sheets

ULTRASONIC IMAGING SYSTEM

FIELD AND BACKGROUND OF THE INVENTION

The present invention relates to ultrasonic imaging systems for imaging an object for the detection of flaws, defects, internal inhomogeneities and the like.

Ultrasonic imaging is used widely for the detection of flaws, defects, internal inhomogeneities and the like in an object, for example, a welded joint. In principle, ultrasonic imaging involves using an ultrasonic probe to transmit a train of ultrasound pulses towards an object, and to receive the echo pulses reflected therefrom. Changes in the amplitude and/or the travel time of the reflected echo pulses are used to image the flaws, defects, internal inhomogeneities and the like in the object. Several techniques of ultrasonic imaging are known in the art, including A-scan imaging on an oscilloscope, B-scan imaging, C-scan imaging and P-scan imaging (G. S. Passi, "Objectivization of the results of ultrasonic inspection of welding seams," *Soviet Journal of Non-destrucrive testing* (English language version). 1987; 23 (6): 372–379; G. S. Passi, "Reducing the influence of human factors on the reliability of manual ultrasonic weld inspection," *Journal of the British Institute of Non-Destructive Testing.* 1995; 37 (10): 788–791; G. S. Passi. "New defect recording system," *Journal of the British Institute of Non-Destructive Testing.* 1996; 38 (4): 260; U.S. Pat. No. 5,524,627—"Ultrasonic imaging system" to Garri S. Passi, issued Jun. 11, 1996.)

A conventional ultrasonic imaging system, generally designated 10, will now be described with reference to FIG. 1. Ultrasonic imaging system 10 includes an ultrasonic probe 12 for transmitting pulses of ultrasonic energy toward an object under test, and for receiving echo pulses reflected therefrom. Ultrasonic probe 12 is typically a hand-held implement for manipulation by an operator. When the surface of the object to be investigated is inaccessible or irregular, such as an object located adjacent to and between two materials (as in the case of the top bead of a weld 14 located between two plates of metal 15 and 17), an angle ultrasonic probe is employed. The operator grips ultrasonic probe 12 and applies its head to adjacent material 15 in proximity to object 14. Acoustic coupling between ultrasonic probe 12 and adjacent material 15 is facilitated by the application of acoustic coupling fluid to the head of ultrasonic probe 12. The operator manipulates ultrasonic probe 12 over adjacent material 15 according to a probe trajectory determined by the type, size and other parameters of the object to be investigated, such that the linear beam of ultrasound pulses emitted from ultrasonic probe 12 enters object 14 via adjacent material 15, and is reflected back to ultrasonic probe 12. Hence, in order to comprehensively detect variously oriented flaws, defects, internal inhomogeneities and the like within object 14, the operator is required to maintain an appropriate rotational orientation, hereinafter referred to as the swiveling angle, of ultrasonic probe 12 with respect to object 14, while manipulating ultrasonic probe 12 along the necessary trajectory on adjacent material 15.

The location of ultrasonic probe 12 on adjacent material 15, as well as the probe swiveling angle, is determined by a probe location monitoring apparatus 16 which provides real time feedback about the actual trajectory of ultrasonic probe 12 on adjacent material 15 to the operator. The probe location monitoring apparatus 16 includes air acoustic emitters 20 and 22 for transmitting signals, and an air acoustic receiver 24 for detecting the signals. The air acoustic emitters are typically integrated with ultrasonic probe 12 via a probe holder 18. The air acoustic receiver 24 is typically in the form of two flat microphones 26 and 28 placed at right angles to one another, so as to provide a Cartesian coordinate system.

The degree of acoustic coupling between ultrasonic probe 12 and adjacent material 15 is monitored by an acoustic coupling monitoring apparatus 30. The acoustic coupling monitoring apparatus includes a low frequency noise vibrator 32, which continuously emits a low frequency noise reference signal into adjacent materials 15 and 17 and object 14. Acoustic coupling monitoring apparatus 30 determines the degree of acoustic coupling by monitoring the amplitude of the low frequency noise reference signal detected by ultrasonic probe 12.

System 10 further includes a digital computer apparatus 34 for manipulating ultrasound echo data and ultrasonic probe 12 position data.

Digital computer apparatus 34 includes a defect image memory 36 for storing data describing defects in object 14 determined by correlating among the amplitude and time delays of echoes received by ultrasonic probe 12, the coordinates and swiveling angle of ultrasonic probe 12 (as determined by probe location monitoring apparatus 16), and the current degree of acoustic coupling (as determined by acoustic coupling monitoring apparatus 30). A defect image display 38 displays the ultrasound scan image of object 14 depicting defects 40 within object 14 by color coding echo amplitude data retrieved from defect image memory 36.

Digital computer apparatus 34 also includes a probe trace memory 42 for storing position data describing the actual trajectory of ultrasonic probe 12 on the surface of adjacent material 15. The actual probe trajectory, depicted in FIG. 1 on the surface of adjacent material 15 for purposes of illustration only and generally designated 44, includes zones 46 of sufficient acoustic coupling between ultrasonic probe 12 and adjacent material 15 and zones 48 which suffer from an insufficient degree of acoustic coupling between ultrasonic probe 12 and adjacent material 15. The data describing the actual probe trace and the areas of insufficient acoustic coupling are provided for storing in probe trace memory 42 by probe location monitoring apparatus 16 and acoustic coupling monitoring apparatus 30. A probe trace display 50 receives data from probe trace memory 42 and displays an image 52 of the actual probe trace 44 with breaks 54 in the trace indicating zones of insufficient acoustic coupling. Probe trace display 50 also generates perceptible signals indicating the current degree of the acoustic coupling, for example, a label 56, and the current location of ultrasonic probe 12 with respect to object 14, for example, a blinking cursor 58.

Turning now to FIG. 2, a part of ultrasonic imaging system 10 is depicted, including angle ultrasonic probe 12 for imaging object 14. Ultrasonic probe 12 typically includes a scanning ultrasonic crystal 60 connected to digital computer apparatus 34 and to the acoustic coupling monitoring apparatus 30, and additional electrical circuitry, such as a matching coil 62, connected to scanning ultrasonic crystal 60. Acoustic coupling monitoring apparatus 30 determines the adequacy of acoustic coupling by monitoring the amplitude of the low frequency reference signal (originating from low frequency noise vibrator 32) detected by scanning ultrasonic crystal 60. Matching coil 62 resonates electrically at a frequency determined by the nature of scanning ultrasonic crystal 60, so as to suppress signals detected by scanning ultrasonic crystal 60 which do not originate from object 14 (arid are thus non-relevant for purposes of defect image imaging), and thus enhance the sensitivity of scanning ultrasonic crystal 60 to relevant signals returning from object 14. Matching coil 62 may alternatively be located in digital computer apparatus 30, rather than in ultrasonic probe 12, but is still connected to scanning ultrasonic crystal 60.

It is well known that the quality and reliability of an ultrasound examination of flaws, defects, and internal inhomogeneities of an object (such as a metal weld) can be adversely affected by a number of factors. Firstly, as the quality of an ultrasound examination is operator dependent, the overall reliability of an examination is determined by the proficiency of the operator at manually manipulating the ultrasonic probe along an ideal scanning trajectory, while maintaining both an adequate ultrasonic probe swiveling angle relative to the object, and an adequate degree of acoustic coupling between the ultrasonic probe and the object under test. In addition, the reliability of the examination is dependent on the degree of accuracy of probe location monitoring apparatus 16.

The ability of the operator to optimize his/her scanning technique is hampered by the following deficiencies of current ultrasonic scanning systems:

1) Although probe trace display 50 of ultrasonic imaging system 10 indicates to the operator when data fallout has occurred due to poor acoustic coupling, and what the location of ultrasonic probe 12 was at such time, it does not inform the operator when data fallout has occurred due to an inadequate probe swiveling angle. This deficiency hampers the operators ability to efficiently rectify all episodes of data fallout.

2) For acoustic coupling monitoring apparatus 30 to be able to reliably assess the adequacy of acoustic coupling at all locations of ultrasonic probe 12 on adjacent materials 15 and 17, it is necessary that adjacent materials 15 and 17 be fully saturated by the low frequency reference noise emitted by low frequency noise vibrator 32. So as to achieve full acoustic saturation of object 14 and adjacent materials 15 and 17, low frequency noise vibrator 32 is required to emit the reference noise at an appropriate minimum power level, this power level being dependent on the size and nature of the materials being scanned, as well as the type of acoustic coupling fluid being used. Acoustic coupling monitoring apparatus 30 of ultrasonic imaging system 10 typically suffers from poor sensitivity to inadequate acoustic coupling conditions because low frequency noise vibrator 32 emits a low frequency reference noise at an arbitrarily fixed power level, which may often be inappropriate for the scanning conditions. As such, the operator may not be made aware of periods of poor acoustic coupling, or may be erroneously informed that acoustic coupling is inadequate, by acoustic coupling monitoring apparatus 30.

3) The reliability with which acoustic coupling monitoring apparatus 30 of ultrasonic imaging system 10 detects adequate acoustic coupling is typically impaired due to partial suppression, by matching coil 62, of the low frequency reference noise detected by scanning ultrasonic crystal 60. As such, the operator may be erroneously informed, by acoustic coupling monitoring apparatus 30, that acoustic coupling is inadequate.

Probe location monitoring apparatus 16 of current ultrasonic imaging systems suffers from the following sources of inaccuracy:

1) Air acoustic receiver 24 (in the form of two flat microphones 26 and 28 placed at right angles to one another) cannot be adjusted to accommodate objects of different sizes for scanning. Small objects are thus scanned using an unnecessarily large Cartesian coordinate system, which decreases the accuracy of position location.

2) Although airborne ultrasound velocity is influenced by environmental conditions such as air temperature, and thus varies with time and location, air acoustic receiver 24 has a fixed, standardized, calibration for airborne ultrasound velocity. As such, air acoustic receiver 24 cannot be recalibrated to the true local ultrasound airborne velocity at the beginning of each ultrasound scan. This limitation decreases the accuracy of the position location mechanism.

3) Air acoustic receiver 24 (in the form of two flat microphones 26 and 28 placed at right angles to one another) allows for inspection of object 14 from one side only (i.e. adjacent material 15). This is because placing ultrasound probe 12 on the other side of object 14 (i.e. on adjacent material 17) inevitably results in the operators hand being positioned between ultrasound probe 12 and flat microphone 26, thus prohibiting reliable position detection by flat microphone 26. Inspection of object 14 from the opposite side, as is typically required by current inspection standards, therefore entails relocating flat microphone 26 to the opposite side of object 14, performing the second ultrasound scan, and then attempting to correlate the data from the two scans. This process is both time consuming and inaccurate.

4) Because air acoustic receiver 24 is made up of flat microphones 26 and 28, the Cartesian reference system created thereby is accordingly flat as well. As such, when air acoustic receiver 24 is used on curved objects, for example welds in pipes, the position data derived from the flat Cartesian reference system is inaccurate.

An additional deficiency in current ultrasound imaging systems is the fact that defect image memory 36 stores only the most recently acquired echo data for each scanned location on object 14. Consequently, echo data of high amplitude, such as that acquired at an acoustically optimal ultrasonic probe location, will be "overwritten" by echo data from the same location on object 14, but of lower amplitude, such as that acquired when the ultrasonic probe was at an acoustically suboptimal location. Defect image display 38 therefore does not necessarily display the best possible image of the defect.

The above deficiencies reduce the reliability and proficiency of conventional ultrasonic imaging system 10. There is therefore a need for an ultrasonic imaging system for imaging objects for the detection of flaws, defects, internal inhomogeneities and the like, which overcomes the deficiencies of conventional ultrasonic imaging systems

SUMMARY OF THE INVENTION

The present invention is an ultrasonic imaging system for the imaging of flaws, defects and inhomogeneities in an object. According to the teachings of the present invention there is provided an ultrasonic imaging system for imaging an object, the system including an ultrasonic probe for scanning the object, a probe location monitoring apparatus for monitoring a trajectory and orientation of the ultrasonic probe with respect to the object, and a mechanism for designating an orientation threshold beyond which the ultrasonic probe does not adequately image the object. The ultrasonic imaging system further includes a trajectory display for displaying the trajectory of the ultrasonic probe, and for providing a perceptible signal indicating when the ultrasonic probe orientation exceeds the orientation threshold beyond which the ultrasonic probe does not adequately image the object.

There is further provided an ultrasonic imaging system for imaging an object, the system including an ultrasonic probe for scanning the object, a probe location monitoring apparatus for monitoring the trajectory and orientation of the ultrasonic probe with respect to the object, and an echo amplitude correction apparatus for selecting a data value from among a plurality of data values representative of the image at one location in the object, such data value corresponding to an ultrasonic signal of largest amplitude.

There is also provided an ultrasonic imaging system for imaging an object with an ultrasonic probe which includes electrical circuitry, the ultrasonic imaging system including a vibrator for generating a reference signal, a detector acoustically coupled to the vibrator for detecting the reference signal, a selector for controlling power output of the vibrator, and an indicator for indicating when the reference signal is being detected by the detector. Further features of the ultrasonic imaging system are that the detector is electrically separated from the electrical circuitry of the ultrasonic probe, and that the detector includes a crystal acoustically coupled to the ultrasonic probe.

There is further provided an ultrasonic imaging system for imaging an object, including an ultrasonic probe for scanning the object and a mechanism for locating the ultrasonic probe by triangulation. This mechanism preferably includes at least two transmitters located on the ultrasonic probe, and at least two transceivers for detecting acoustic signals emitted by the transmitters. It is a further feature of the ultrasonic imaging system that one of the transceivers is displaceable with respect to a second of the transceivers, and that the system includes mechanisms for designating a displacement between the transceivers and a degree of curvature of the object being imaged.

There is further provided a method for verifying an acoustic coupling of an ultrasonic probe to a workpiece, including the steps of: introducing a reference signal into the workpiece, using a vibrator having an adjustable power output level; providing a detector, acoustically coupled to the probe, for detecting the reference signal; and adjusting the power output level so that the detector detects the reference signal. Preferably, the reference signal includes low frequency noise, and the adjusting is effected by placing the ultrasonic probe on the workpiece, as far as is practicable from the vibrator, and gradually raising the power output level of the vibrator until the detector detects the reference signal.

BRIEF DESCRIPTION OF THE DRAWINGS

The invention is herein described, by way of example only, with reference to the accompanying drawings, wherein.

DESCRIPTION OF THE PREFERRED EMBODIMENTS

The present invention is an ultrasonic imaging system for imaging objects for the detection of flaws, defects, internal inhomogeneities and the like.

The principles of operation of the ultrasonic imaging system, according to the teachings of the present invention, may be better understood with reference to the drawings and the accompanying description.

Figure 1:
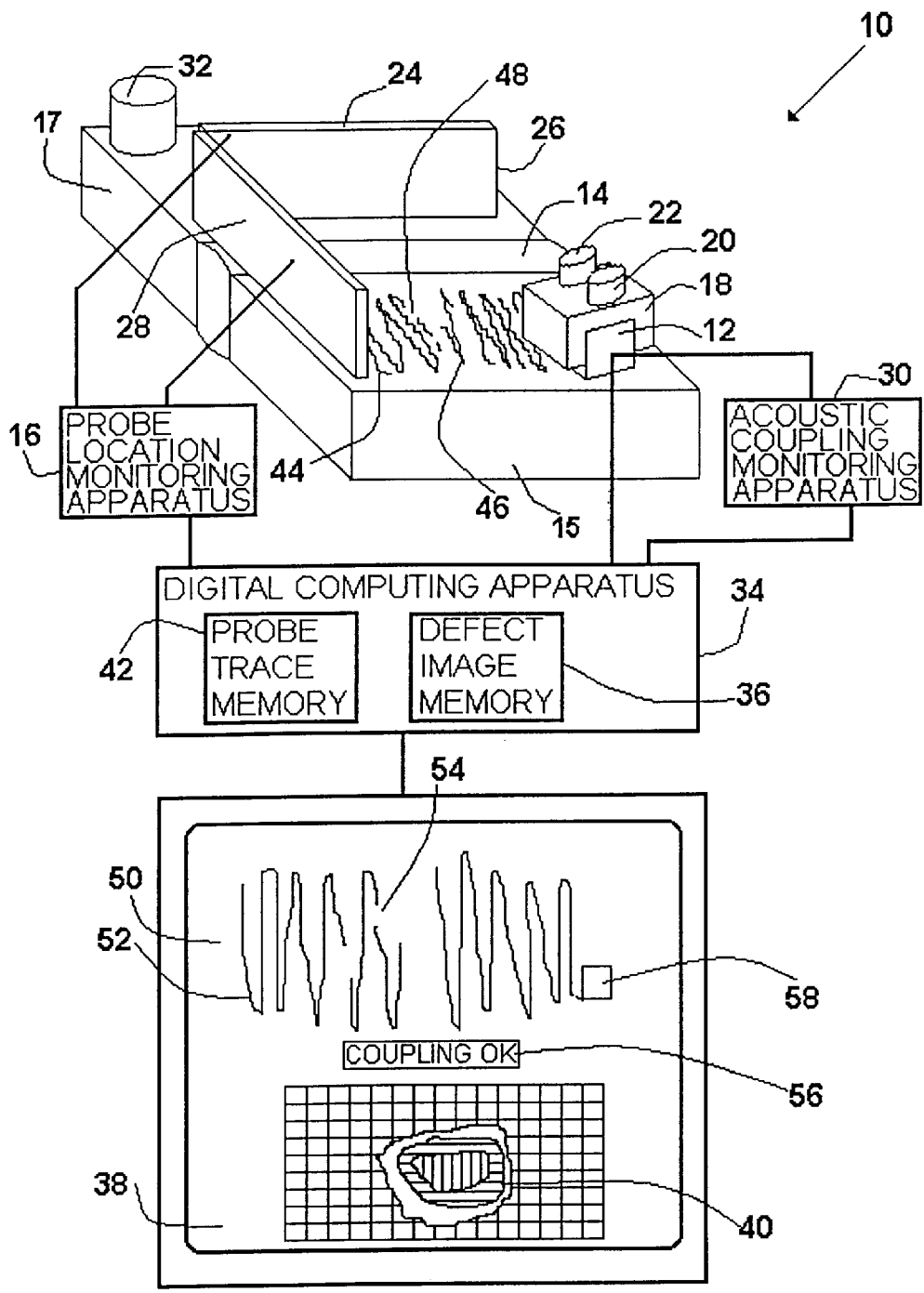
FIG. 1 is a schematic illustration, partially in perspective, of a conventional ultrasonic imaging system.
Figure 2:
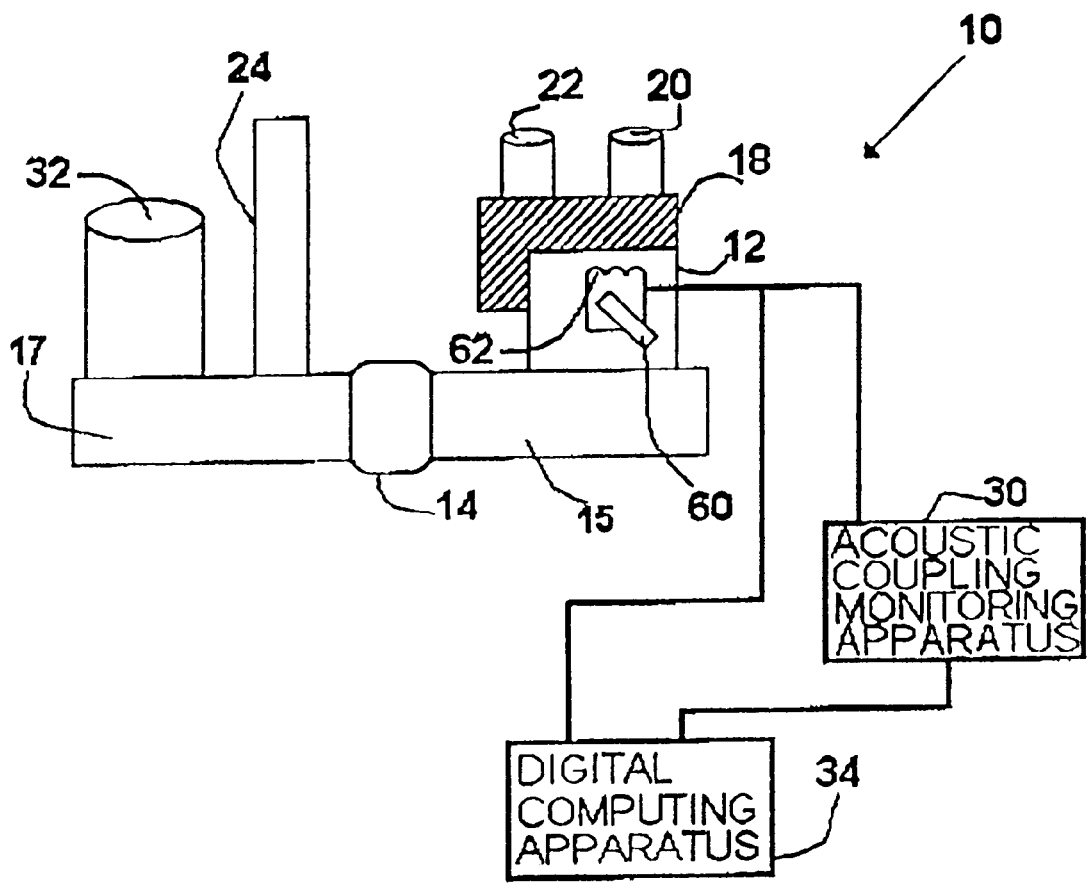
FIG. 2 is a partial schematic illustration, in cross section, of the conventional ultrasonic imaging system of FIG. 1, including an angle ultrasonic probe with a scanning ultrasonic crystal and matching coil.
Figure 3:
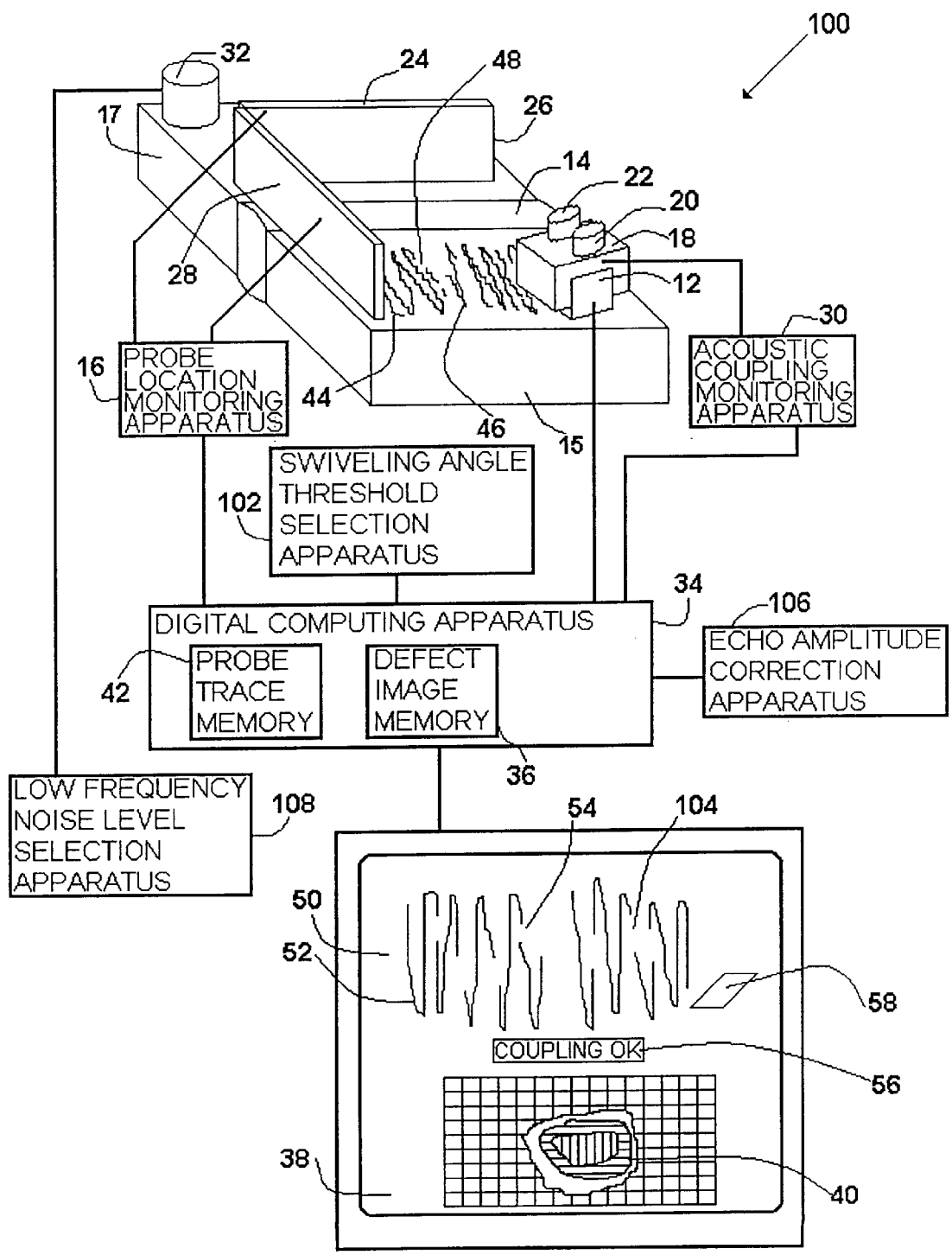
FIG. 3 is a schematic illustration, partially in perspective, of a first embodiment of an ultrasonic imaging system for imaging an object, according to the teachings of present invention.

Referring now to the drawings, FIG. 3 illustrates a first preferred embodiment of an ultrasonic imaging system of the present invention, generally designated 100, constructed and operative according to the teachings of the present invention, for imaging objects for the detection of flaws, defects, internal inhomogeneities and the like. Ultrasonic imaging system 100 is similar to ultrasonic imaging system 10 and therefore common elements are denoted with similar reference numbers used to describe ultrasonic imaging system 10.

Hence, ultrasonic imaging system 100 includes ultrasonic probe 12 for imaging object 14, probe location monitoring apparatus 16 for providing the location and swiveling angle of ultrasonic probe 12 relative to object 14, and probe holder 18 for integrating probe location monitoring apparatus 16 with ultrasonic probe 12. Furthermore, system 100 includes acoustic coupling monitoring apparatus 30 for measuring the degree of acoustic coupling between ultrasonic probe 12 and adjacent material 15.

System 10 further includes digital computer apparatus 34, including defect image memory 36 for storing image data and displaying images of defects in object 14 on defect image display 38, and probe trace memory 42 for storing probe position data and displaying a trace, on probe trace display 50, describing the actual trajectory of ultrasonic probe 12 on the surface of adjacent material 15.

It is a particular feature of system 100 that it further includes a swiveling angle threshold selection apparatus 102. Swiveling angle threshold selection apparatus 102 stores the value of a predetermined ultrasound probe orientation threshold, for example, a swiveling angle of ultrasound probe 12 with respect to object 14, deemed to be appropriate for object 14 being examined. The value of such swiveling angle threshold is manually entered into swiveling angle threshold apparatus 102 by the operator prior to commencing the ultrasound examination. During ultrasound scanning of object 14, digital computing apparatus 34 compares the actual swiveling angle of ultrasonic probe 12, retrieved from probe location monitoring apparatus 16, with the predetermined swiveling angle threshold, retrieved from swiveling angle threshold selection apparatus 102. When digital computing apparatus 34 determines that the actual probe swiveling angle exceeds the predetermined threshold, thus resulting in echo data fallout, such data along with the corresponding position data determined by probe location monitoring apparatus 16 is input to probe trace memory 42, and subsequently displayed on probe trace display 50 as a perceptible signal indicating to the operator that data fallout has occurred due to an inadequate swiveling angle of ultrasonic probe 12. Such an indication may be in the form of a change occurring in the shape of blinking cursor 58, corresponding to the current location of ultrasonic probe 12 with respect to object 14. Image 52 of the actual probe trajectory 44 displayed on probe trace display 50 will show a break 104 in the tracing, indicating a zone of data fallout. Having such an indication, the operator can return ultrasonic probe 12 to the corresponding zones on adjacent material 15 and repeat the scanning providing appropriate acoustic coupling and swiveling angle.

It is a further feature of system 100 that it includes echo amplitude correction apparatus 106. Echo amplitude correction apparatus 106 compares the amplitude of currently acquired echo data depicting a defect 40 at a particular location in object 14, with data already stored in defect image memory 36 depicting the same defect 40 at the same location in object 14, such already stored data having been previously acquired when ultrasonic probe 12 was positioned at a different location or swiveling angle to the current location or swiveling angle. If echo amplitude correction apparatus 106 determines that the current echo amplitude is less than the already stored echo amplitude, then the current echo amplitude value is normalized to that of the already stored echo amplitude value prior to being stored in defect image memory 36, whereas if the current echo amplitude is greater than the already stored echo amplitude, the already stored echo amplitude is overwritten by the current amplitude in defect image memory 36. As such, the image of defect 40 displayed by defect image display 38, after retrieving display data from defect image memory 36, is the best possible image of the defect that can be displayed based on echo data acquired at any time during the current examination.

It is a still further feature of system 100 that it includes a low frequency noise level selection apparatus 108, connected to low frequency noise vibrator 32, for manually selecting the power at which the low frequency reference noise will be generated by low frequency noise vibrator 32. An example of a mechanism allowing for the power output of an oscillator to be manually determined, which is suitable to be used as a low frequency noise level selection apparatus 108, includes a digital to analog converter, for example, a DAC 0830 (National Semiconductors, USA). The operator determines the appropriate power output for low frequency noise vibrator 32 by placing an excessive amount of couplant between ultrasonic probe 12 and adjacent material 15, positioning ultrasonic probe 12 on adjacent material 15 at a point distant from object 14, initiating functioning of low frequency noise vibrator 32 at maximum power output by appropriately adjusting low frequency noise level selection apparatus 108 to the maximum power output setting, and then gradually decreasing the power output of low frequency noise vibrator 32 until such time as acoustic coupling label 56 indicates that acoustic coupling is inadequate. The power output level of low frequency noise vibrator 32 is then minimally increased and set at such a level as to provide a stable indication of adequate acoustic coupling by label 56 on probe trace display 50.

Figure 4:
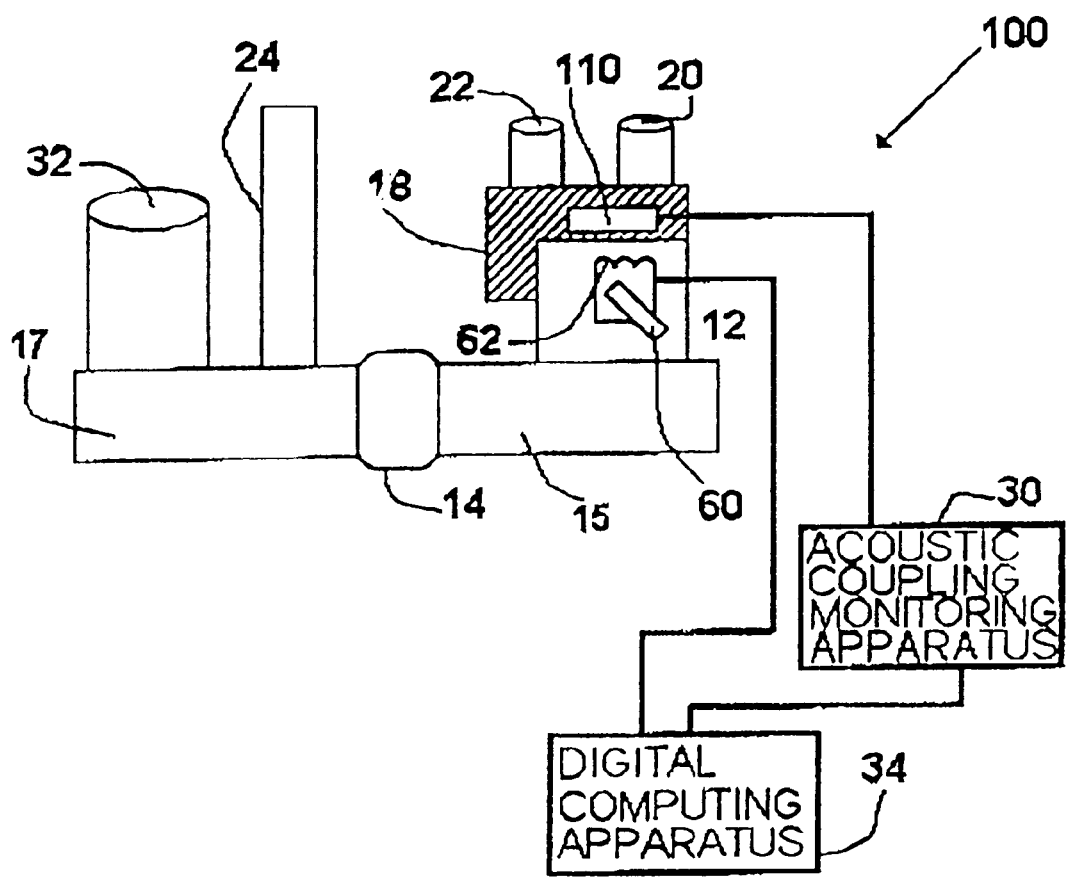
FIG. 4 is a partial schematic illustration, in cross section, of the first embodiment of an ultrasonic imaging system of FIG. 3.

Turning now to FIG. 4, ultrasonic imaging system 100 further includes a low frequency noise receiving crystal 110 located in probe holder 18 (i.e. not connected to matching coil 62), for detecting the low frequency reference noise saturating object 14 and adjacent materials 15 and 17, and relaying such data to acoustic coupling monitoring apparatus 30. As there is mechanical coupling between the casing of ultrasonic probe 12 and probe holder 18, the low frequency noise saturating object 14 and adjacent materials 15 and 17 is transmitted to low frequency noise receiving crystal 110 via the casing of ultrasonic probe 12. Acoustic coupling monitoring apparatus 30 is connected directly to low frequency noise receiving crystal 110 only, and not to scanning ultrasonic crystal 60 or matching coil 62. As such, suppression of the low frequency noise reference signal by matching coil 62 does not inhibit the detection of adequate acoustic coupling by acoustic coupling monitoring apparatus 30.

Figure 5:
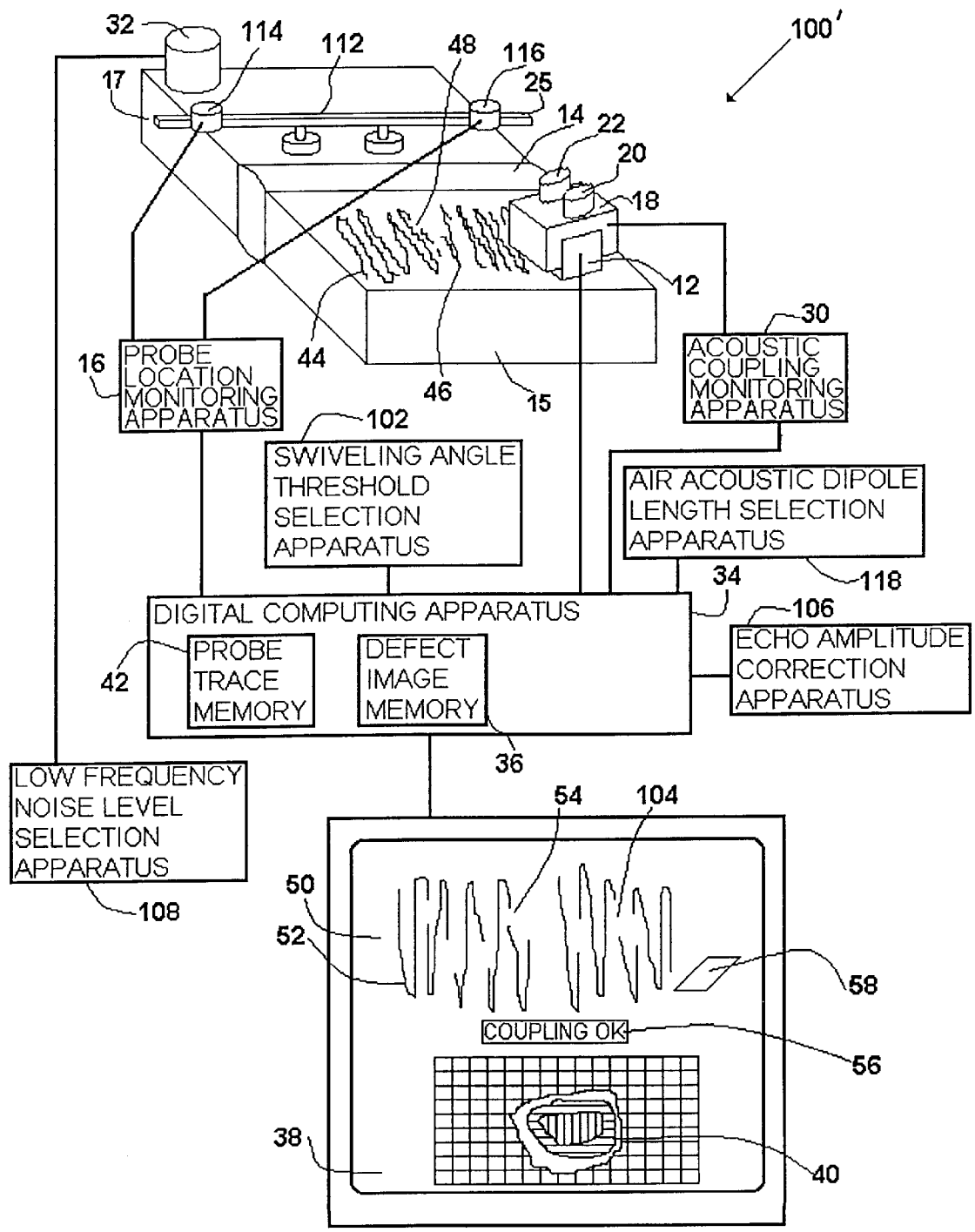
FIG. 5 is a schematic illustration, partially in perspective, of a second embodiment of an ultrasonic imaging system for imaging an object, according to the teachings of present invention.
Figure 6:
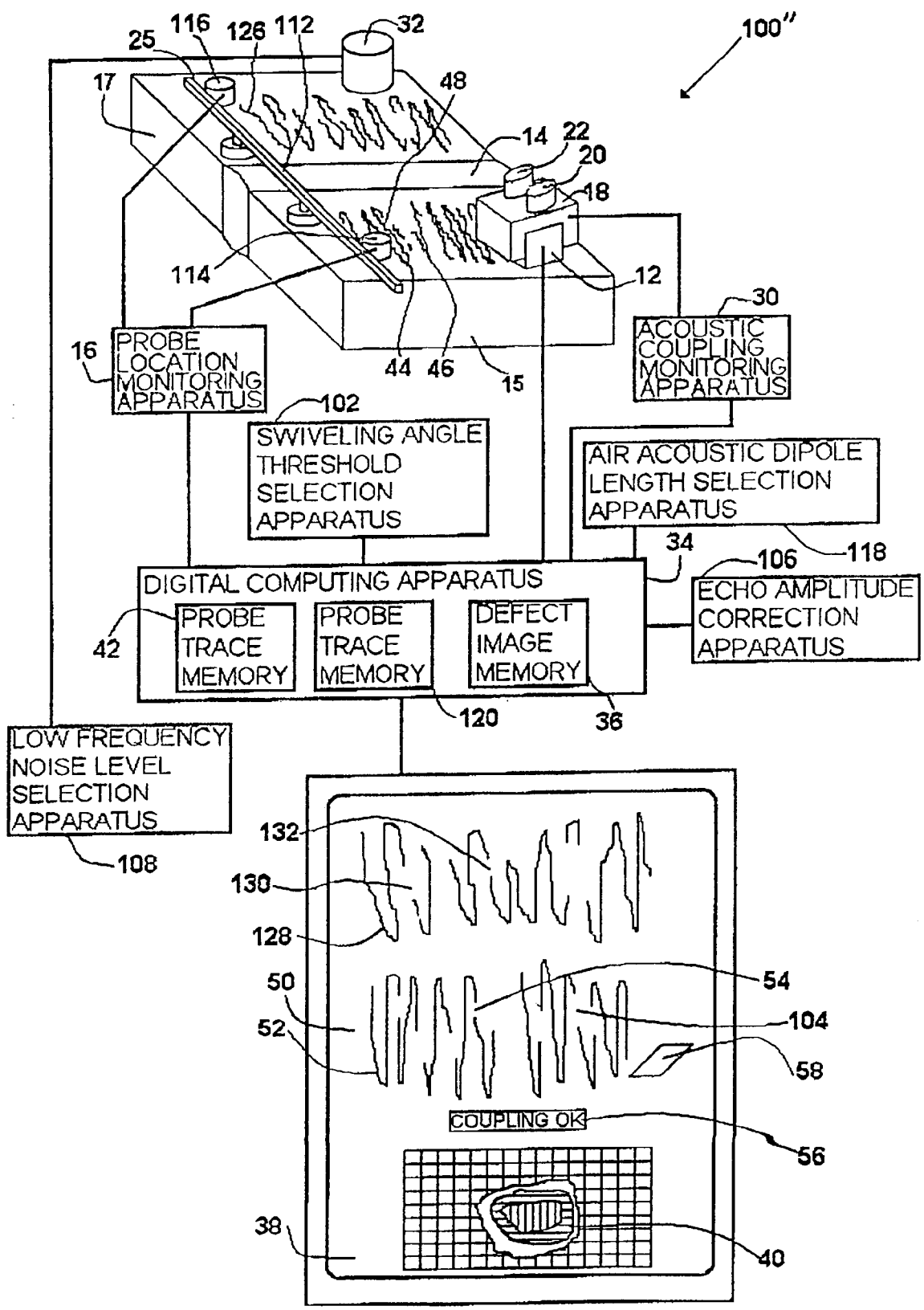
FIG. 6 is a schematic illustration, partially in perspective, of a third embodiment of an ultrasonic imaging system for imaging an object, showing the probe location monitoring apparatus straddling the object being scanned so as to facilitate scanning of both sides of the object.

Turning now to FIG. 5, a second embodiment 100' of the ultrasonic imaging system of the present invention is shown, in which probe location monitoring apparatus 16 includes an air acoustic receiver 25 in the form of an air acoustic dipole, consisting of two mobile non-directional transceivers 114 and 116 (each being, for example, a poled through wall piezo-electric tube, Keramos Inc. Indianapolis, Ind.) capable of both emitting and receiving acoustic signals (such as those emitted by air acoustic emitters 20 and 22), and a dipole supporting rail 112 upon which non-directional transceivers 114 and 116 are mounted and along which non-directional transceivers 114 and 116 can be slid. To provide digital computing apparatus 43 with the distance between the two non-directional transceivers 114 and 116, ultrasonic imaging system 100' further includes an air acoustic dipole length selection apparatus 118. Prior to commencing the ultrasound examination, the operator manually enters data defining the distance between the two non-directional transceivers 114 and 116 into air acoustic dipole length selection apparatus 118. Air acoustic receiver 25 is placed on adjacent material 17, in such a location as to allow for triangulation of ultrasonic probe 12 with non-directional transceivers 114 and 116, thus establishing a Cartesian coordinate system for monitoring ultrasonic probe 12 position location and swiveling angle by probe location monitoring apparatus 16, as shown in FIG. 5. Similarly, air acoustic receiver 25 can be placed straddling object 14 so as to create a single Cartesian coordinate system encompassing areas on both adjacent materials 15 and 17, while still enabling the operators hand to remain distant from the acoustic pathway between air acoustic emitters 20 and 22, and air acoustic receiver 25. This arrangement allows for the performance of an ultrasound examination of object 14 from both sides (i.e. both from adjacent material 15 and adjacent material 17), as illustrated in FIG. 6, without having to reposition air acoustic receiver 25. As the distance between non-directional transceivers 114 and 116 is easily adjustable, the dimensions of the Cartesian coordinate system can be tailored to the size of object 14 being examined, thus improving the accuracy of position data generated by probe location monitoring apparatus 16. Furthermore, as the distance between non-directional transceivers 114 and 116 is known and is stored in air acoustic dipole length selection apparatus 118, the true air ultrasound velocity can be easily calculated by digital computing apparatus 34 as described as follows. Probe location monitoring apparatus 16 measures the time of flight of an acoustic signal emitted from one non-directional transceiver 114 and received by a second non-directional transceiver 116. Digital computing apparatus 34 then correlates this value with data retrieved front air acoustic dipole length selection apparatus 118 describing the distance between non-directional transceivers 114 and 116, so as to calculate the true air ultrasound velocity. This air ultrasound velocity value is then used by digital computing apparatus 34 when computing position data for ultrasonic probe 12 based on data retrieved from probe location monitoring apparatus 16.

Turning now to FIG. 6, a third embodiment 100" of the ultrasonic imaging system of the present invention is shown in which digital computing apparatus 34 includes an additional probe trace memory 120, for storing position data describing the actual trajectory of ultrasonic probe 12 on the opposite side of object 14 (i.e. the surface of adjacent material 17) in instances in which object 14 is examined from both sides during the course of a single ultrasound examination. Probe trace memory 120 is identical in structure and function to probe trace memory 42. The data describing the actual probe trace and the areas of insufficient acoustic coupling or inadequate swiveling angle are provided for storing in probe trace memory 120 by probe location monitoring apparatus 16 and acoustic coupling monitoring apparatus 30. As such, probe trace display 50 displays both actual probe traces 44 and 126 by retrieving data from both probe trace memories 42 and 120 simultaneously. Images 52 and 128 of probe traces 44 and 126 include breaks 54 and 130 caused by inadequate acoustic coupling and breaks 104 and 132 caused by an inadequate swiveling angle of ultrasonic probe 12. Although images of two probe traces are displayed on probe trace display 50 simultaneously, only one perceptible signal corresponding to the current degree of the acoustic coupling, for example label 56, and only one perceptible signal corresponding to the current adequacy of the swiveling angle, for example blinking cursor 58 with a changeable shape, are displayed.

Figure 7:
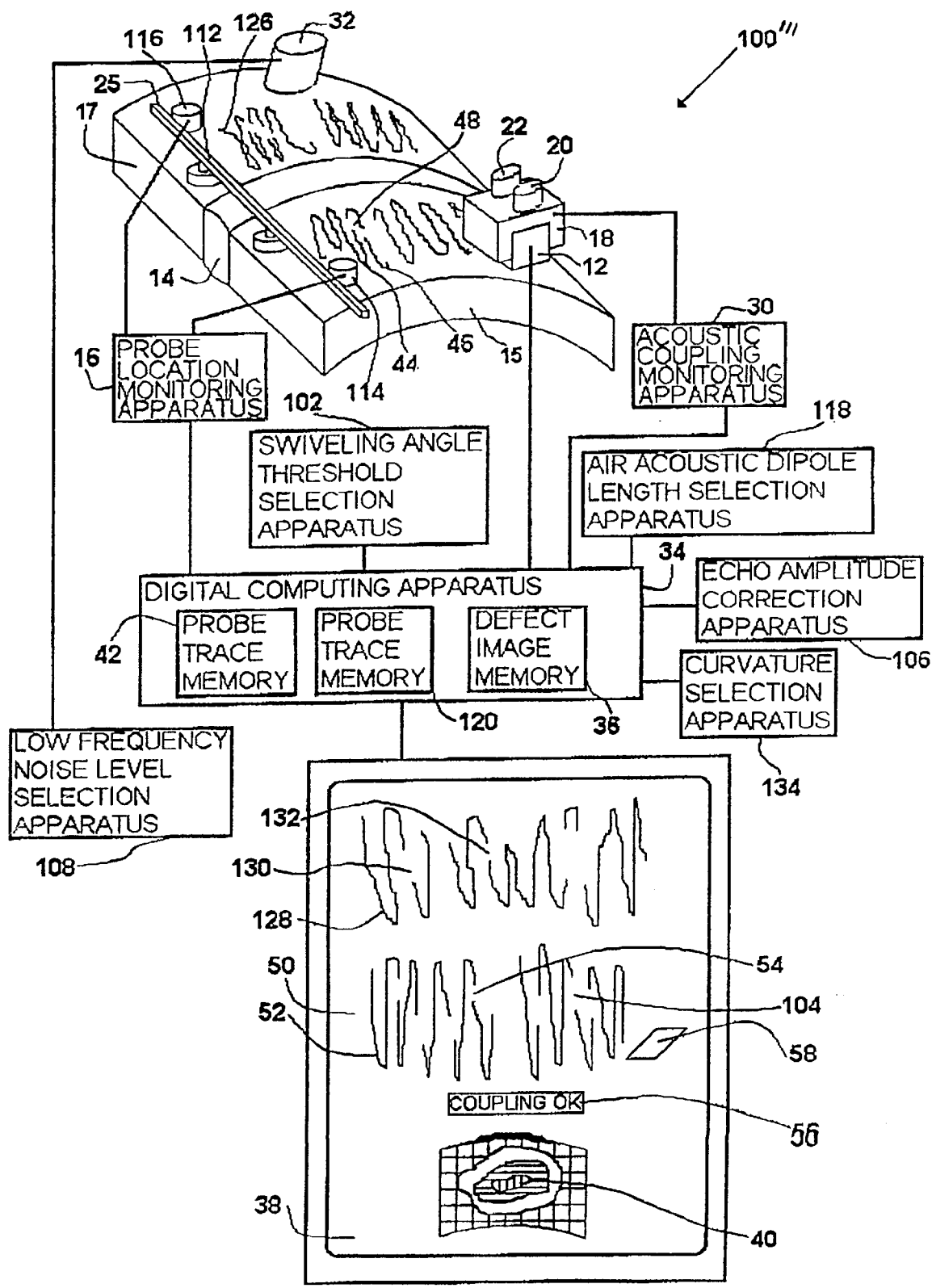
FIG. 7 is a schematic illustration, partially in perspective, of a fourth embodiment of an ultrasonic imaging system for imaging an object, in which the object being imaged is curved.

Turning now to FIG. 7, a system 100''' of the present invention further includes a curvature selection apparatus 134 for storing data defining the curvature radius of object 14 when, for example, object 14 is the curved butt weld between two pipes, and air acoustic receiver 25 is placed straddling object 14 such that support rail 112 does not lie along the radius of curvature itself, but rather lies on the long axis of the pipe being examined. In this circumstance, the radius of curvature of object 14 is retrieved by digital computing apparatus 34 from curvature selection apparatus 134, and used to translate the linear distance between ultrasonic probe 12 and non-directional transceivers 114 and 116, as input into digital computing apparatus 34 by probe location monitoring apparatus 16, into a circumferential "surface" distance by expressing the linear distance as a chord between two points of a cylindrical surface. As such, ultrasonic imaging system 100''' is able to accurately determine the position of ultrasonic probe 12, and thus accurately describe the location of any defects 40, when examining a circumferential object.

In summary, therefore, and as compared with prior ultrasonic imaging systems, the current invention provides the operator with more accurate and reliable information about the adequacy of acoustic coupling between the ultrasonic probe and the object being imaged; facilitates the maintenance, by the operator, of an optimal ultrasonic probe orientation with respect to the object being imaged; produces better quality images of any defects within objects being imaged; allows for the accurate imaging of curved objects; allows for more accurate imaging of objects of different sizes; allows for the imaging of an object from both of its sides without the need to relocate the entire imaging system; and allows for more accurate imaging of objects under environmental conditions which influence air ultrasound velocity.

While the invention has been described with respect to a limited number of embodiments, it will be appreciated that many variations, modifications and other application of the invention may be made.

What is claimed is:

1. An ultrasonic imaging system for imaging an object, the system comprising:
   (a) an ultrasonic probe for scanning the object;
   (b) a probe location monitoring apparatus for monitoring a trajectory and orientation of said ultrasonic probe with respect to the object; and
   (c) a mechanism for receiving, as an input into the system, a definition of an orientation threshold beyond which said ultrasonic probe will not adequately image the object.

2. The ultrasonic imaging system of claim 1, further comprising a trajectory display for displaying said trajectory of said ultrasonic probe, wherein said trajectory display provides a perceptible signal inditing when said ultrasonic probe is oriented at an orientation exceeding said defined orientation threshold received as an input into the system.

3. An ultrasonic imaging system for imaging an internal inhomogeneity in an object, the system comprising:
   (a) an ultrasonic probe for scanning the object;
   (b) a probe location monitoring apparatus for monitoring a trajectory and orientation of said ultrasonic probe with respect to the object;
   (c) a monitor for displaying an image of the internal inhomogeneity in the object, said image being a graphic representation of ultrasound signals which have been reflected off of, and are representative of, the internal inhomogeneity in the object, and
   (d) an echo amplitude correction apparatus for selecting for display, on said monitor, an ultrasound signal of greatest amplitude, wherein said ultrasoun signal of greatest amplitude is selected from amongst a plurality of said reflected ultrasound signals representative of the internal inhomogeneity, and wherein said ultrasound signal of greatest amplitude is displayed on said monitor instead of an ultrasound signal of lesser amplitude representative of the same internal inhomogeneity.

4. An ultrasonic imaging system for imaging an object with an ultrasonic probe including electrical circuitry, the system comprising:
   (a) a vibrator for generating a reference signal;
   (b) a detector, acoustically coupled to the ultrasonic probe, for detecting said reference signal;
   (c) a selection apparatus for gradually varying a power output of said vibrator, said selection apparatus being operative to vary said power output between more than two power output gradations, and
   (d) an indicator for indicating when said reference signal is being detected by said detector.

5. The system as in claim 4, wherein said detector is electrically separated from the electrical circuitry of the ultrasonic probe.

6. The system as in claim 4, wherein said detector includes a crystal acoustically coupled to the ultrasonic probe.

7. An ultrasonic imaging system for imaging an object, comprising:
   (a) an ultrasonic probe for scanning the object, said ultrasonic probe including at least two transmitters for transmission of air acoustic signals; and
   (b) an acoustic dipole for locating said ultrasonic probe by triangulation, said acoustic dipole including two non-directional acoustic transceivers for detecting said air acoustic signals transmitted by said transmitters.

8. The system as in claim 7, wherein a first of said transceivers is displaceable with respect to a second of said transceivers.

9. The system as in claim 8, further including a mechanism for designating a displacement between said transceivers.

10. The system as in claim 7, further including a mechanism for designating a degree of curvature of the object.

11. A method for verifying an acoustic coupling of an ultrasonic probe to a workpiece, comprising the steps of:
   (a) introducing a reference signal into the workpiece, using a vibrator having a gradually adjustable power output level;
   (b) providing a detector, acoustically coupled to the probe, for detecting said inference signal;
   (c) providing a mechanism for indicating when said reference signal is detected by said detector; and
   (d) gradually increasing said power output level through a plurality of gradations until said mechanism indicates that said reference signal is detected by said detector.

12. The method of claim 11, further comprising the step of:
   (e) positioning the probe at a substantially maximal distance on the workpiece from said vibrator.

13. The method of claim 11, wherein said reference signal includes low frequency noise.

* * * * *